(12) United States Patent
Bera et al.

(10) Patent No.: US 9,380,956 B2
(45) Date of Patent: Jul. 5, 2016

(54) METHOD AND APPARATUS FOR CLASSIFYING CARDIAC ARRHYTHMIA

(71) Applicant: Samsung Electronics Co., Ltd., Suwon-si (KR)

(72) Inventors: Deep Bera, Bangalore (IN); Raghavendra Bobbi Shankarnarayana Bhatta, Shimoga District (IN); Rangavittal Narayanan, Bangalore (IN); Sandipan Chakroborty, Bangalore (IN); Praveen Pankajakshan, Bangalore (IN)

(73) Assignee: Samsung Electronics Co., Ltd., Suwon-si (KR)

( * ) Notice: Subject to any disclaimer, the term of this patent is extended or adjusted under 35 U.S.C. 154(b) by 918 days.

(21) Appl. No.: 13/629,963

(22) Filed: Sep. 28, 2012

(65) Prior Publication Data
US 2013/0085405 A1  Apr. 4, 2013

(30) Foreign Application Priority Data

Sep. 28, 2011 (IN) .......................... 3378/CHE/2011
Sep. 28, 2012 (KR) ........................ 10-2012-0108669

(51) Int. Cl.
*A61B 5/0456* (2006.01)
*A61B 5/044* (2006.01)
(Continued)

(52) U.S. Cl.
CPC ............. *A61B 5/044* (2013.01); *A61B 5/0006* (2013.01); *A61B 5/04012* (2013.01); *A61B 5/04014* (2013.01); *A61B 5/0452* (2013.01);
(Continued)

(58) Field of Classification Search
CPC ............ A61B 5/0452; A61B 5/04525; A61B 5/0456; A61B 5/046; A61B 5/044; A61B 5/04012

USPC .......................................... 600/515, 516, 517
See application file for complete search history.

(56) References Cited

U.S. PATENT DOCUMENTS

| | | | |
|---|---|---|---|
| 5,658,317 A | 8/1997 | Haefner et al. | |
| 5,819,007 A * | 10/1998 | Elghazzawi | A61B 5/0452 600/515 |
| 5,957,857 A | 9/1999 | Hartley | |
| 6,169,919 B1 | 1/2001 | Nearing et al. | |
| 6,480,734 B1 | 11/2002 | Zhang et al. | |
| 7,027,858 B2 | 4/2006 | Cao et al. | |

(Continued)

FOREIGN PATENT DOCUMENTS

| | | |
|---|---|---|
| EP | 2 327 360 A1 | 6/2011 |
| JP | 8-206089 A | 8/1996 |
| KR | 10-1998-0008168 A | 4/1998 |

OTHER PUBLICATIONS

Lee, K. Y. et al. (Nov. 2006). "A Eliminating Method for Baseline Wander Using Ascending Slope Tracing waves in ECG." *Trans. KIEE.* vol. 55D, No. 11:pp. 471-475; 5 pages including English translation of abstract.

*Primary Examiner* — Theodore Stigell
*Assistant Examiner* — Michael Carey
(74) *Attorney, Agent, or Firm* — NSIP Law (57) ABSTRACT

A method and a device for classifying cardiac arrhythmia, using an electrocardiogram (ECG) signal, are provided. The method includes receiving the ECG signal representing an electrical activity of a heart of an individual over a period of time, the ECG signal including ECG beats. The method further includes converting each of the ECG beats into symbols. The method further includes identifying an arrhythmia class indicating a type of cardiac arrhythmia associated with the individual from arrhythmia classes indicating respective types of cardiac arrhythmia based on the symbols representing each of the ECG beats.

21 Claims, 10 Drawing Sheets

(51) Int. Cl.
*A61B 5/0452* (2006.01)
*A61B 5/04* (2006.01)
*A61B 5/00* (2006.01)

(52) U.S. Cl.
CPC ........... *A61B5/0456* (2013.01); *A61B 5/04525* (2013.01); *A61B 5/7267* (2013.01)

(56) References Cited

U.S. PATENT DOCUMENTS

| | | | |
|---|---|---|---|
| 7,272,436 | B2 | 9/2007 | Gill et al. |
| 2006/0052717 | A1 | 3/2006 | Mugler et al. |
| 2012/0283569 | A1* | 11/2012 | Ciompi ................ A61B 8/0891 600/463 |

* cited by examiner

METHOD AND APPARATUS FOR CLASSIFYING CARDIAC ARRHYTHMIA

CROSS-REFERENCE TO RELATED APPLICATION(S)

This application claims the benefit under 35 U.S.C. §119(a) of India Provisional Application No. 3378/CHE/2011 filed on Sep. 28, 2011, in the Indian Patent Office, and of Korean Patent Application No. 10-2012-0108669, filed on Sep. 28, 2012, in the Korean Intellectual Property Office, the entire disclosures of which are incorporated herein by reference for all purposes.

BACKGROUND

1. Field

The following description relates to a method and an apparatus for classifying cardiac arrhythmia.

2. Description of Related Art

An electrocardiogram (ECG) system monitors electrical activity of a heart of a patient. A normal electrocardiogram includes a P wave, a QRS complex, a T wave, and a U wave. An ECG analysis is a method of studying functions of a heart of a patient, and identifying disorders of the heart.

Doctors have been using ECG systems to monitor a patient's heart activity. There are several different systems that analyze ECG signals to monitor electrical activity of a patient's heart, and identify a type of cardiac arrhythmia that the patient is suffering. However, these systems are stationary, and are not suitable for portable use.

SUMMARY

In one general aspect, there is provided a method of classifying cardiac arrhythmia, using an electrocardiogram (ECG) signal, the method including receiving the ECG signal representing an electrical activity of a heart of an individual over a period of time, the ECG signal including ECG beats. The method further includes converting each of the ECG beats into symbols. The method further includes identifying an arrhythmia class indicating a type of cardiac arrhythmia associated with the individual from arrhythmia classes indicating respective types of cardiac arrhythmia based on the symbols representing each of the ECG beats.

In another general aspect, there is provided a health monitoring device including a communication interface configured to receive an electrocardiogram (ECG) signal representing an electrical activity of a heart of an individual over a period of time, the ECG signal including ECG beats. The health monitoring device further includes an arrhythmia classification module configured to convert each of the ECG beats into symbols. The arrhythmia classification module is further configured to identify an arrhythmia class indicating a type of cardiac arrhythmia associated with the individual from arrhythmia classes indicating respective types of cardiac arrhythmia based on the symbols representing each of the ECG beats.

In still another general aspect, there is provided a system including an acquisition device configured to generate an electrocardiogram (ECG) signal representing an electrical activity of a heart of an individual over a period of time, the ECG signal including ECG beats. The system further includes a health monitoring device configured to convert each of the ECG beats into symbols. The health monitoring device is further configured to identify an arrhythmia class indicating a type of cardiac arrhythmia associated with the individual from arrhythmia classes indicating respective types of cardiac arrhythmia based on the symbols representing each of the ECG beats.

Other features and aspects may be apparent from the following detailed description, the drawings, and the claims.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

Figure 1A:
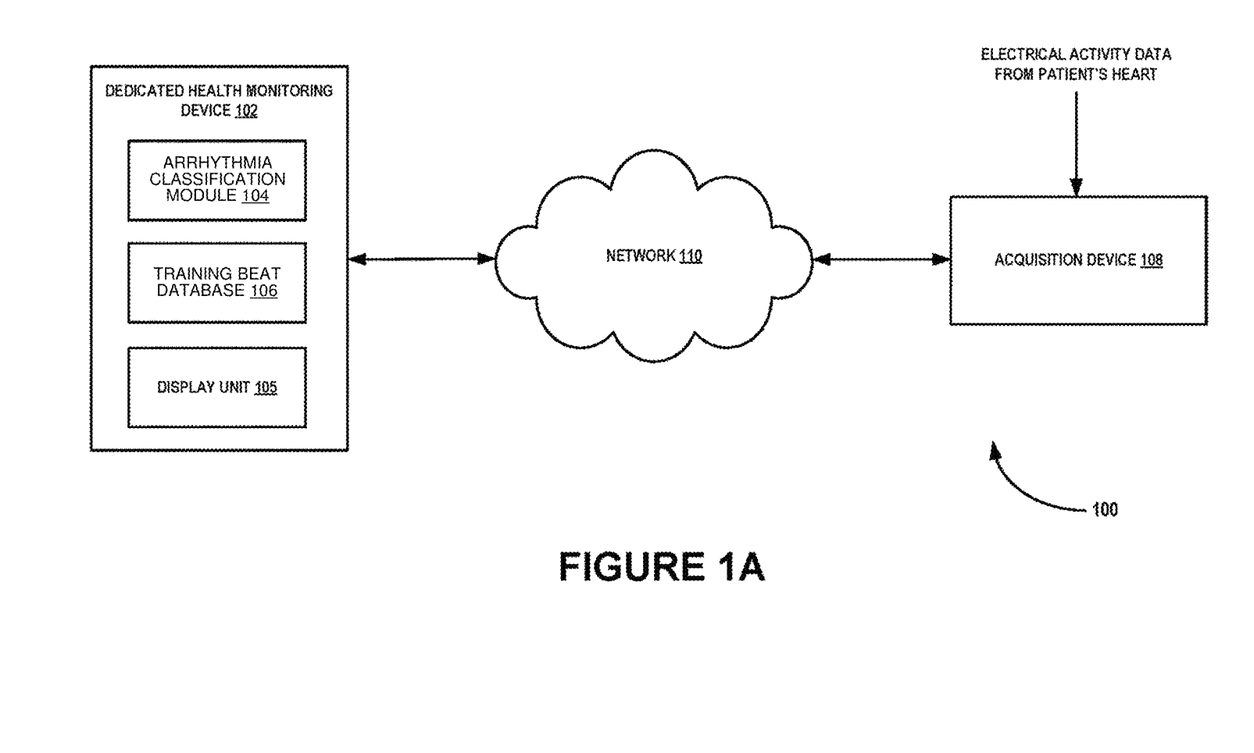
FIG. 1A is a block diagram illustrating an example of a health monitoring environment.

FIG. 1A is a block diagram illustrating an example of a health monitoring environment 100. In FIG. 1A, the health monitoring environment includes a dedicated health monitoring device 102 and an acquisition device 108. The acquisition device 108 includes a device coupled to one or more sensors disposed on a body of an individual (i.e., patient) suffering from cardiac disorder. The dedicated health monitoring device 102 includes an electronic device that is wirelessly connected to the acquisition device 108 via a wireless network 110. In an example, the dedicated health monitoring device 102 may be provided to a doctor responsible for monitoring heart activity of the patient. For example, the dedicated health monitoring device 102 may include a smartphone or a tablet PC that is associated with the doctor. In another example, the dedicated health monitoring device 102 may be provided to an attendant associated with the patient. In this example, the dedicated health monitoring device 102 may include a handheld device provided to the attendant by hospital authorities. As shown, the health monitoring device 102 includes an arrhythmia classification module 104, a training beat database 106, and a display unit 105.

The acquisition device 108 periodically collects electric activity data of a heart of the individual from the sensors disposed on the body of the individual, and generates an ECG signal based on the electric activity data. Thereafter, the acquisition device 108 transmits the electric activity data via the ECG signal to the dedicated health monitoring device 102 over the wireless network 110. The ECG signal received at the health monitoring device 102 includes ECG beats, each of which representing an electrical activity of the heart over a cardiac cycle. The arrhythmia classification module 104 filters the ECG signal, using a band pass filter, and detects a R-peak in each ECG beat of the ECG signal. The arrhythmia classification module 104 segments a region of each ECG beat that is around the respective R-peak, and converts the region of each ECG beat into symbolic aggregate approximation (SAX) symbols.

The arrhythmia classification module 104 retrieves training beats corresponding to respective arrhythmia classes indicating respective types of arrhythmia from the training beat database 106. The arrhythmia classes may include normal, left bundle brunch block, right bundle brunch block, atrial premature beat, and/or premature ventricular contraction. Thereafter, the arrhythmia classification module 104 identifies an arrhythmia class indicating a type of arrhythmia associated with the individual by comparing the SAX symbols representing each ECG beat and SAX symbols representing each training beat. The arrhythmia classification module 104 displays the arrhythmia class to a user via the display unit 105.

Figure 1B:
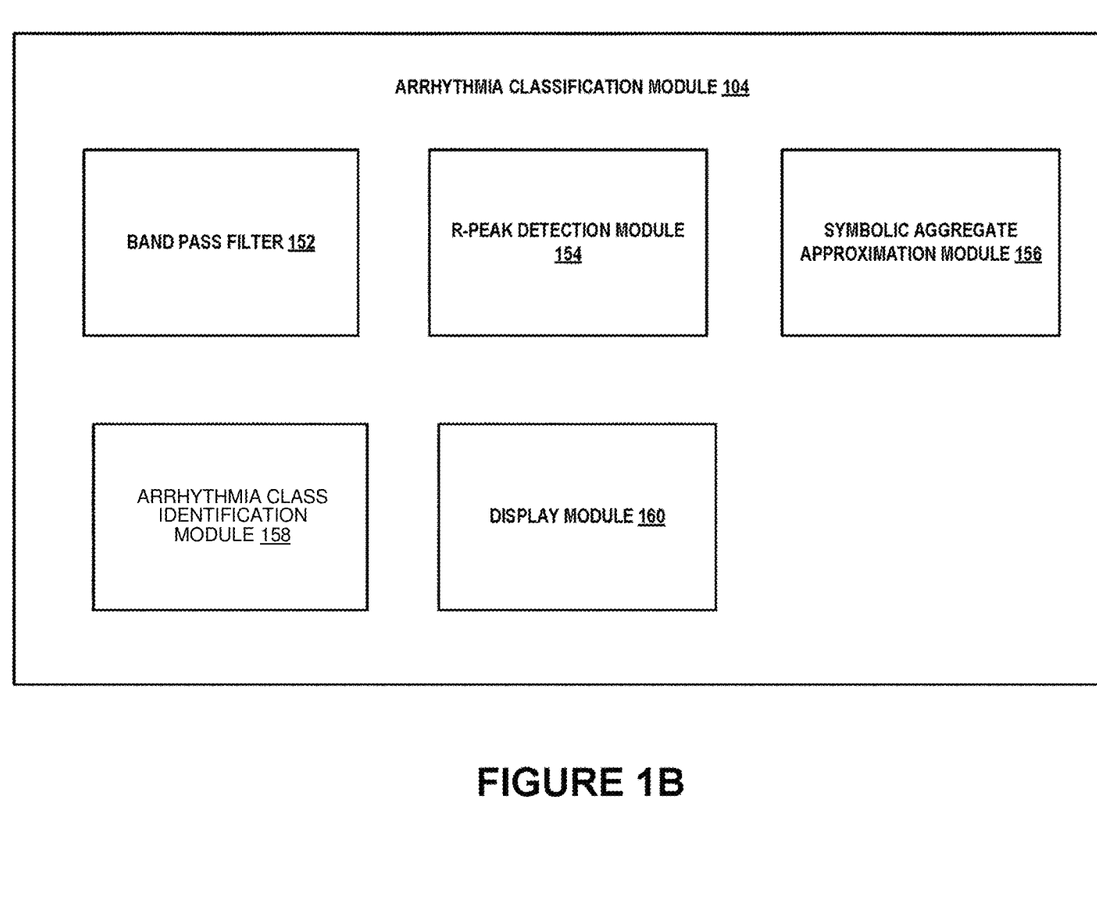
FIG. 1B is a block diagram illustrating an example of an arrhythmia classification module of FIG. 1A.

FIG. 1B is a block diagram illustrating an example of the arrhythmia classification module 104 of FIG. 1A. In FIG. 1B, the arrhythmia classification module 104 includes a band pass filter 152, a R-peak detection module 154, a symbolic aggregate approximation module 156, an arrhythmia class identification module 158, and a display module 160.

The band pass filter 152 filters the ECG signal representing the electrical activity of the heart of the individual, using a high pass filter and a low pass filter. The R-peak detection module 154 detects a location of the R-peak in each ECG beat of the ECG signal.

The symbolic aggregate approximation module 156 segments the region of each ECG beat that is around the respective R-peak. The symbolic aggregate approximation module 156 converts the region of each ECG beat into the SAX symbols.

The arrhythmia class identification module 158 identifies the arrhythmia class indicating the type of cardiac arrhythmia associated with the individual from the arrhythmia classes. In an example, the arrhythmia classification module 158 identifies the arrhythmia class based on a morphology similarity measure technique, as will be explained in the description of FIG. 3. In another example, the arrhythmia classification module 158 identifies the arrhythmia class based on a K-mean clustering technique, as will be explained in the description of FIG. 4. The display module 160 displays the arrhythmia class to the user via the display unit 105 of FIG. 1A.

Figure 2:
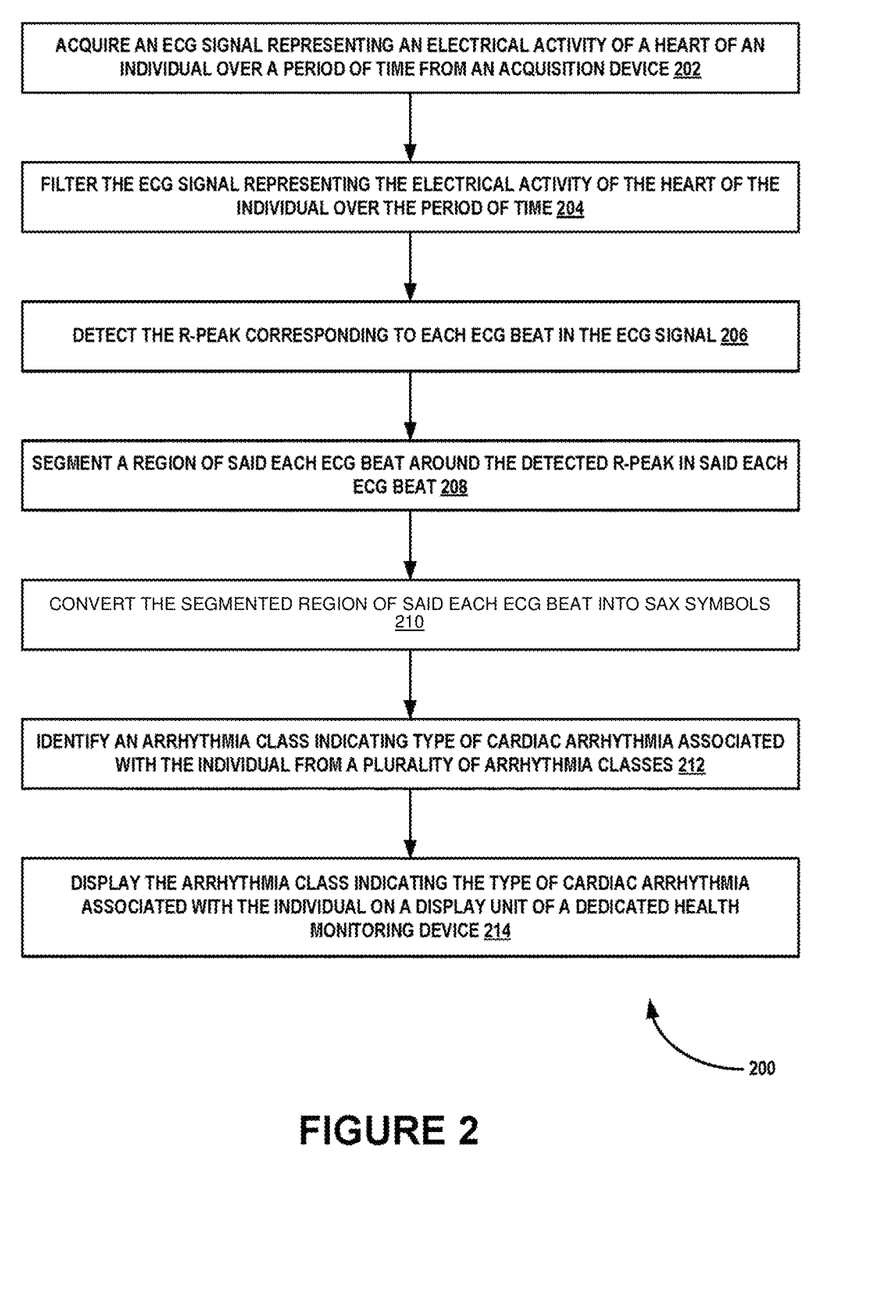
FIG. 2 is a flowchart illustrating an example of a method of classifying an arrhythmia based on an electrocardiogram (ECG) signal.

FIG. 2 is a flowchart illustrating an example of a method 200 of classifying an arrhythmia based on an ECG signal. For example, the method may be performed by the arrhythmia classification module 104 of FIGS. 1A and 1B.

At step 202, the ECG signal representing an electrical activity of a heart of an individual over a period of time is acquired from an acquisition device, e.g., the acquisition device 108 of FIG. 1A. The ECG signal includes ECG beats. At step 204, the ECG signal representing the electrical activity of the heart of the individual over the period of time is filtered. For example, the ECG signal may be filtered using a band pass filter with cutoff frequencies of 0.5 Hz and 40 Hz. In more detail, the ECG signal may be filtered using a high pass filter with a cutoff frequency of 0.5 Hz, and a low pass filter with a cutoff frequency of 40 Hz. At step 206, the R-peak corresponding to each ECG beat in the ECG signal is detected. The method of detecting the R-peak is described in greater detail in the description of FIG. 6.

Figure 8A:
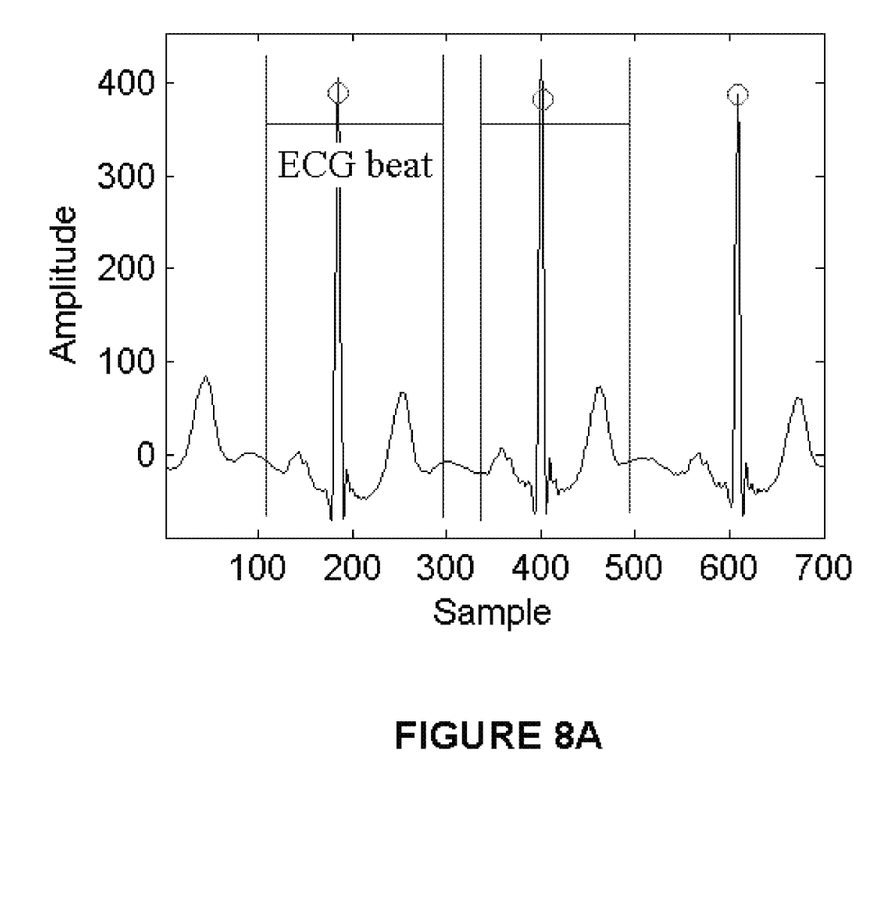
FIG. 8A is a graph illustrating an example of segmentation of ECG beats of an ECG signal.

At step 208, a region of said each ECG beat around the detected R-peak in said each ECG beat is segmented. The region of each ECG beat is segmented by moving in a backward direction and a forward direction around the R-peak. Referring to FIG. 8A, a detected R-peak in each ECG beat is circled, and a region of each ECG beat around the respective detected R-peak is shown by lines. At step 210, the segmented region of said each ECG beat is converted into SAX symbols. SAX is an approximation technique that allows dimensionality reduction along with a lower bound on the $L^p$ norm. A time series T of a length n may be represented in a w-dimensional space (where w<<n) by a vector $\overline{T} = \overline{t}_1, \ldots, \overline{t}_w$. An $i^{th}$ element of the vector T may be determined based on Equation 1:

$$\overline{T}_i = \frac{w}{n} \sum_{j=\frac{n}{w}(i-1)+1}^{\frac{n}{w}i} T_j \tag{1}$$

To convert the time series T of the length n into a string of an arbitrary length w, the ECG beat is divided into w equal-sized windows. For each window, a mean value is determined. A vector of mean values of the respective windows is a representation in a reduced dimension. This representation is known as a Piecewise Aggregate Approximation (PAA). After the conversion of the time series T into the PAA, further approximation is applied for discretization. The discretization helps produce symbols with equal probability. Normalized subsequences may include a highly Gaussian distribution. Therefore, "breakpoints" that may produce equal areas under a Gaussian curve may be easily determined Breakpoints $B = \beta_1, \ldots, \beta_{a-1}$ are a list of sorted numbers such that an area under a N(0, 1) Gaussian curve from $\beta_i$ to $\beta_{i+1} = 1/a$ (where $\beta_0$ and $\beta_a$ are defined as $-\infty$ and $\infty$, respectively). These breakpoints B may be determined from a statistical table. For values of a from 3 to 5, Table 1 shows breakpoints $\beta_1$ to $\beta_4$.

TABLE 1

| $\beta_i$ | a = 3 | a = 4 | a = 5 |
|---|---|---|---|
| $\beta_1$ | −0.43 | −0.67 | −0.84 |
| $\beta_2$ | 0.43 | 0 | −0.25 |
| $\beta_3$ | | 0.67 | 0.25 |
| $\beta_4$ | | | 0.84 |

Figure 8B:
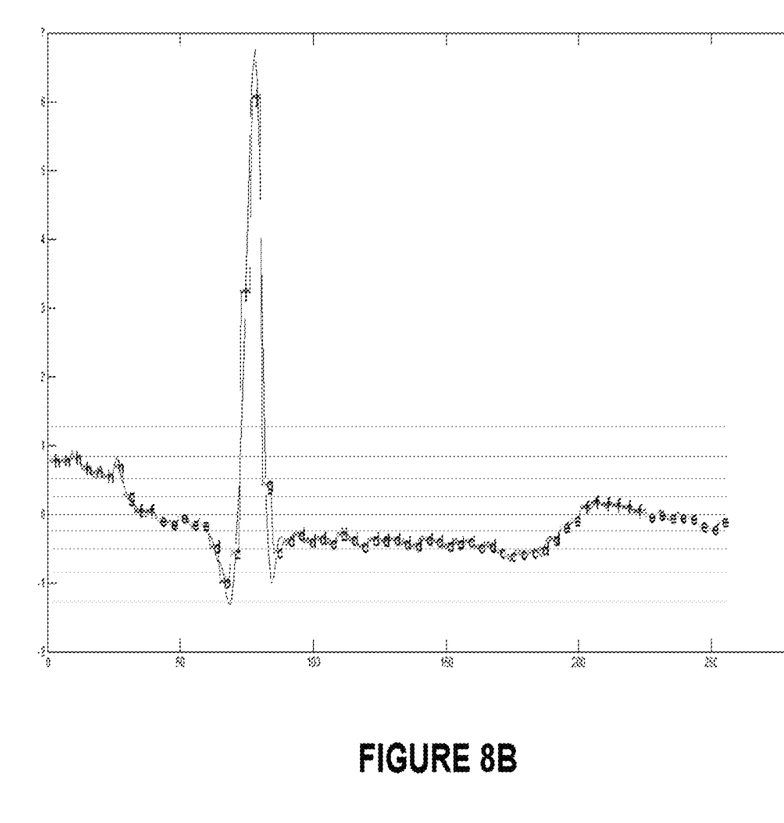
FIG. 8B is a graph illustrating an example of symbolic aggregate approximation (SAX) symbolization of an ECG beat.

After determining the breakpoints, the discretization of the time series is performed. Coefficients of the PAA that are less than the smallest breakpoint are mapped to a symbol "a", the coefficients that are greater than or equal to the smallest breakpoint are mapped to a symbol "b", and so on. Referring to FIG. 8B, eight symbols "b", "c", "d", "e", "f", "g", "h", and "j" may be used to represent an original time series. A concatenation of the SAX symbols symbolizing a sequence is termed as a word.

At step 212, an arrhythmia class indicating a type of cardiac arrhythmia associated with the individual from a plurality of arrhythmia classes is identified by comparing the SAX symbols representing each ECG beat and SAX symbols representing training beats stored in, e.g., the training beat database 106 of FIG. 1A. The training beats correspond to the respective arrhythmia classes indicating respective types of arrhythmia. At step 214, the arrhythmia class indicating the type of cardiac arrhythmia associated with the individual is displayed on a display unit of a dedicated health monitoring device, e.g., the display unit 105 of the dedicated health monitoring device 102 of FIG. 1A.

Figure 3:
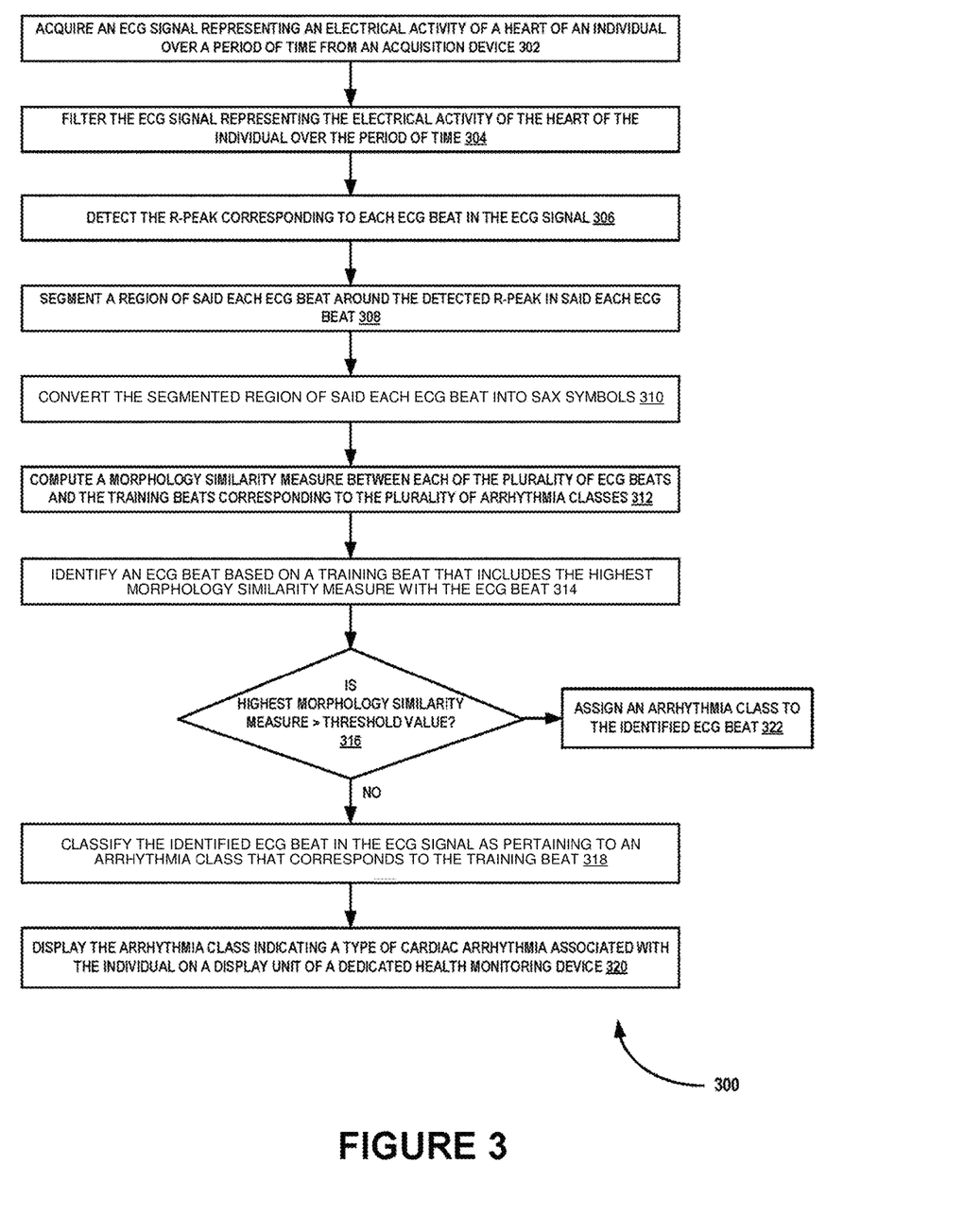
FIG. 3 is a flowchart illustrating another example of a method of classifying an arrhythmia based on an ECG signal.

FIG. 3 is a flowchart illustrating another example of a method 300 of classifying an arrhythmia based on an ECG signal. For example, the method may be performed by the arrhythmia classification module 104 of FIGS. 1A and 1B.

At step 302, the ECG signal representing an electrical activity of a heart of an individual over a period of time is acquired from an acquisition device, e.g., the acquisition device 108 of FIG. 1A. The ECG signal includes a plurality of ECG beats. At step 304, the ECG signal representing the electrical activity of the heart of the individual over the period of time is filtered. At step 306, the R-peak corresponding to each ECG beat in the ECG signal is detected.

At step 308, a region of said each ECG beat around the detected R-peak in said each ECG beat is segmented. At step 310, the segmented region of said each ECG beat is converted into SAX symbols. At step 312, a morphology similarity measure is computed between each of the plurality of ECG beats and the training beats corresponding to the plurality of arrhythmia classes indicating respective types of arrhythmia. In more detail, a MINDIST function is used to compute the morphology similarity measure between each of the ECG beats and the training beats. The MINDIST function returns a minimum distance between an original time series of two words (e.g., an ECG beat and a training beat) based on Equation 2:

$$MINDIST(\bar{P}, \bar{Q}) \equiv \sqrt{\frac{n}{w}} \sqrt{\sum_{i}^{w} dist(\hat{p}_i, \hat{q}_i)^2} \quad (2)$$

In Equation 2, $\bar{P}$ and $\bar{Q}$ denote the two words whose morphology similarity measure is to be determined, and $\hat{p}_i$ and $\hat{q}_i$, denote SAX symbols of the two words $\bar{P}$ and $\bar{Q}$, respectively. A sub-function dist( ) may be implemented using a lookup table shown in Table 2.

TABLE 2

|   | a | b | c | d |
|---|---|---|---|---|
| a | 0 | 0 | 0.67 | 1.34 |
| b | 0 | 0 | 0 | 0.67 |
| c | 0.67 | 0 | 0 | 0 |
| d | 1.34 | 0.67 | 0 | 0 |

At step 314, an ECG beat is identified from the plurality of ECG beats in the ECG signal based on a training beat that includes the highest morphology similarity measure (the lowest MINDIST value) with the ECG beat. At step 316, it is determined whether the highest morphology similarity measure associated with the identified ECG beat is greater than a predetermined threshold value. If it is determined that the highest morphology similarity measure is less than the threshold value, then at step 318, the identified ECG beat in the ECG signal is classified as pertaining to an arrhythmia class that corresponds to the training beat associated with the highest morphology similarity measure. Additionally, the arrhythmia class that corresponds to the training beat is identified as an arrhythmia class indicating a type of cardiac arrhythmia associated with the individual. At step 320, the arrhythmia class indicating a type of arrhythmia associated with the individual is displayed on a display unit of a dedicated health monitoring device, e.g., the display unit 105 of the dedicated health monitoring device 102 of FIG. 1A. If it is determined that the highest morphology similarity measure is greater than the threshold value, then at step 322, an arrhythmia class indicating a type of arrhythmia is assigned to the identified ECG beat. Additionally, the identified ECG beat assigned with the arrhythmia class indicating the type of arrhythmia is stored in, e.g., the training beat database 106.

Figure 4:
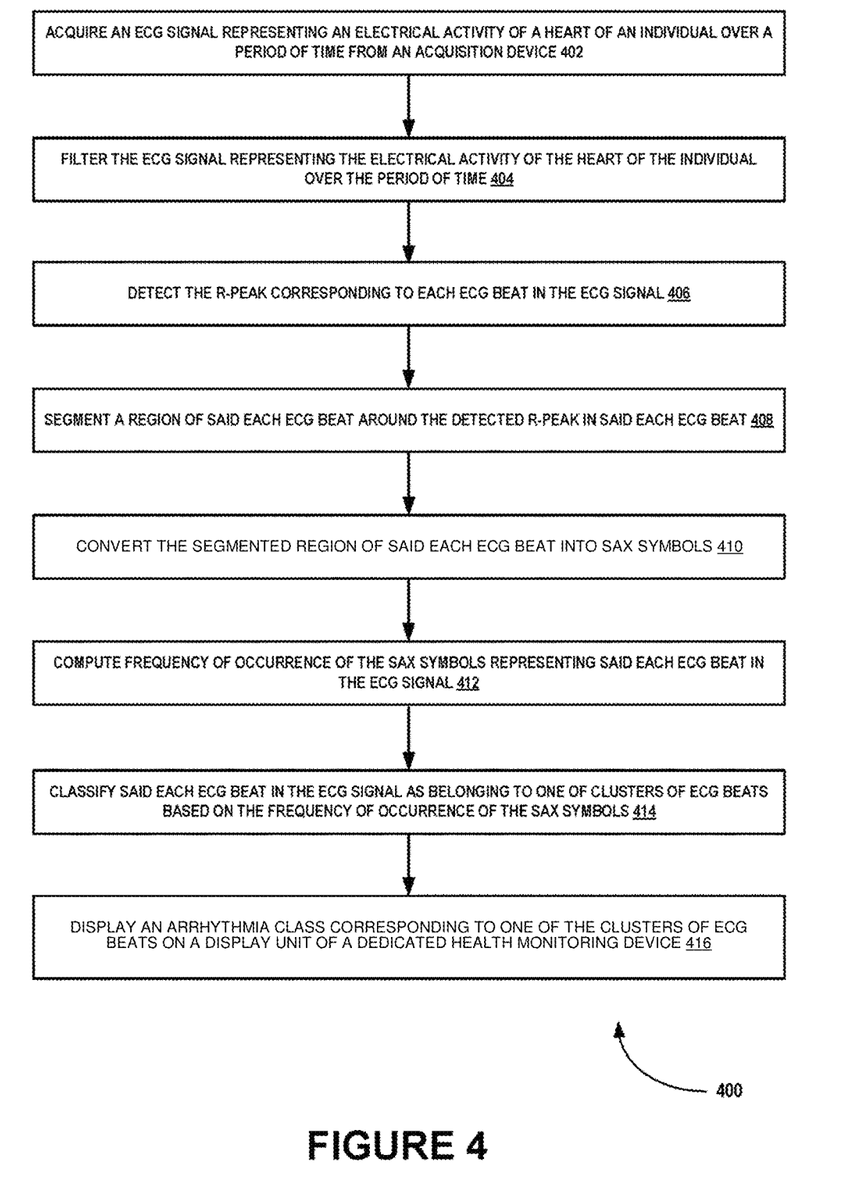
FIG. 4 is a flowchart illustrating still another example of a method of classifying an arrhythmia based on an ECG signal.

FIG. 4 is a flowchart illustrating still another example of a method 400 of classifying an arrhythmia based on an ECG signal. For example, the method may be performed by the arrhythmia classification module 104 of FIGS. 1A and 1B.

At step 402, the ECG signal representing an electrical activity of a heart of an individual over a period of time is acquired from an acquisition device, e.g., the acquisition device 108 of FIG. 1A. The ECG signal includes ECG beats. At step 404, the ECG signal representing the electrical activity of the heart of the individual over the period of time is filtered. At step 406, the R-peak corresponding to each ECG beat in the ECG signal is detected.

At step 408, a region of said each ECG beat around the detected R-peak in said each ECG beat is segmented. At step 410, the segmented region of said each ECG beat is converted into SAX symbols. At step 412, a normalized frequency of occurrence of the SAX symbols representing said each ECG beat in the ECG signal is computed. At step 414, said each ECG beat in the ECG signal is classified as belonging to one of clusters of ECG beats based on the frequency of occurrence of the SAX symbols. Additionally, an arrhythmia class corresponding to one of the clusters of ECG beats is identified as an arrhythmia class indicating a type of cardiac arrhythmia associated with the individual. For example, each ECG beat may be classified into any one of three different clusters or groups, such as Normal ECG beats, premature ventricular contraction (PVC) ECG beats, and atrial premature complex (APC) ECG beats. At step 416, the arrhythmia class corresponding to one of the clusters of ECG beats is displayed on a display unit of a dedicated health monitoring device, e.g., the display unit 105 of the dedicated health monitoring device 102 of FIG. 1A.

Figure 5:
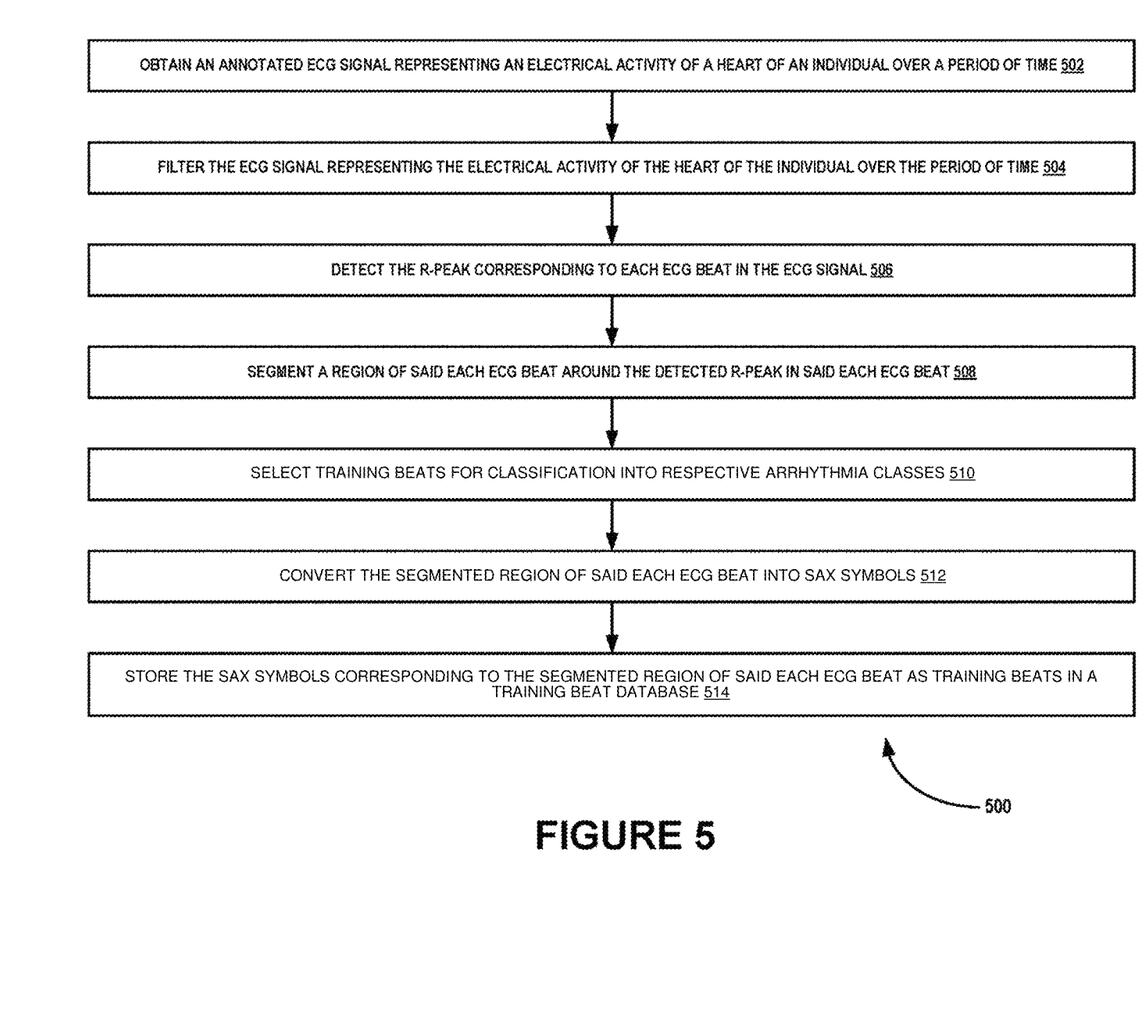
FIG. 5 is a flowchart illustrating an example of a method of constructing a training beat database including a number of training beats.

FIG. 5 is a flowchart illustrating an example of a method 500 of constructing a training beat database including a number of training beats. For example, the method may be performed by the arrhythmia classification module 104 of FIGS. 1A and 1B.

At step 502, an annotated ECG signal representing an electrical activity of a heart of an individual over a period of time is obtained from, e.g., the acquisition device 108 of FIG. 1A. At step 504, the ECG signal representing the electrical activity of the heart of the individual over the period of time is filtered. At step 506, the R-peak corresponding to each ECG beat in the ECG signal is detected.

At step 508, a region of said each ECG beat around the detected R-peak in said each ECG beat is segmented. At step 510, training beats are selected for classification into respective arrhythmia classes. For example, the training beats may include a Normal (N) beat, a Premature Ventricular Contraction (V) beat, an Atrial Premature (A) beat, a Junctional Premature Contraction (J) beat, a Junctional Escape (j) beat, and/or a Ventricular Escape (E) beat. At step 512, the segmented region of said each ECG beat is converted into SAX symbols. At step 514, the SAX symbols corresponding to the segmented region of said each ECG beat are stored as training beats in a training beat database.

Figure 6:
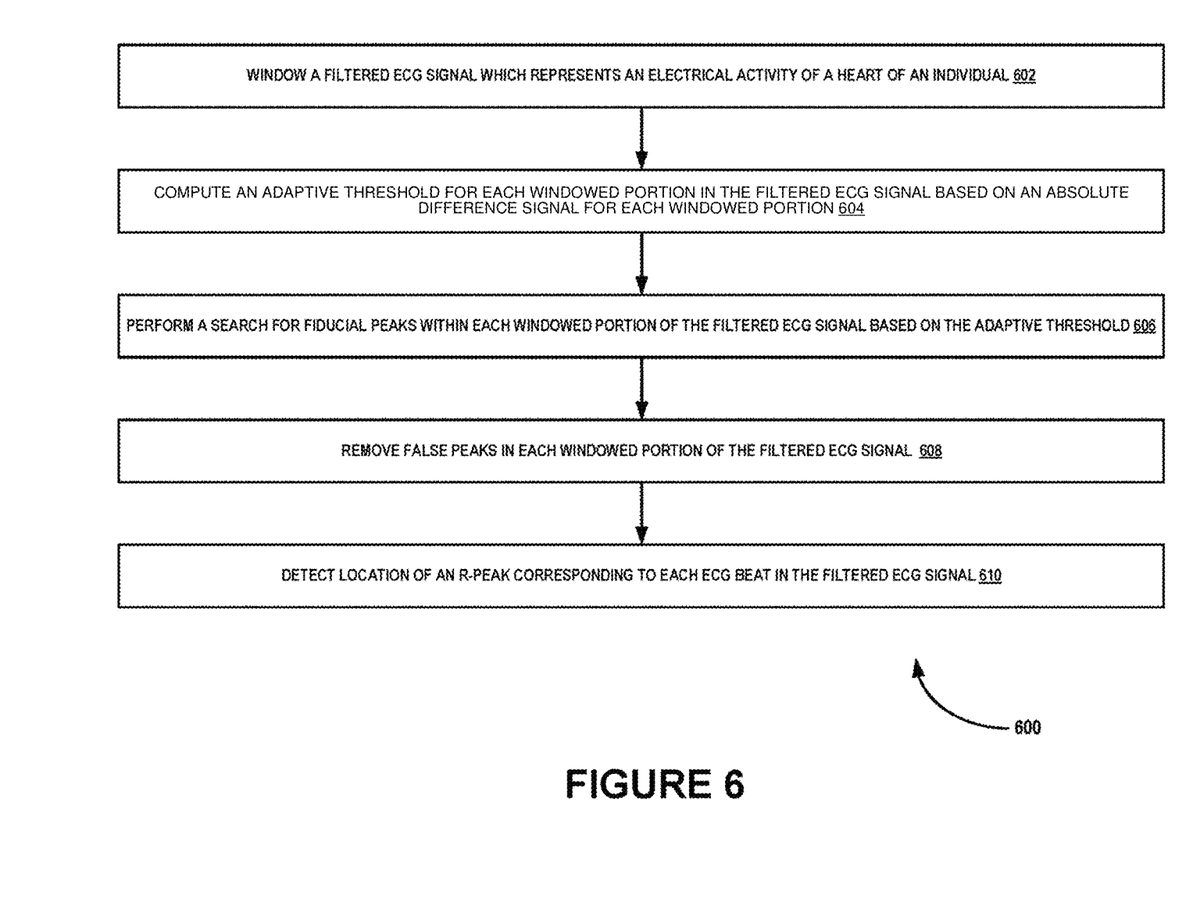
FIG. 6 is a flowchart illustrating an example of a method of detecting a R-peak in each ECG beat of an ECG signal.

FIG. 6 is a flowchart illustrating an example of a method 600 of detecting a R-peak in each ECG beat of an ECG signal. For example, the method may be performed by the R-peak detection module 154 of FIG. 1B.

At step 602, a filtered ECG signal representing an electrical activity of heart of an individual is windowed into portions. The filtered ECG signal may be denoted as $x_0[n]$, and the ECG signal may be sampled with a sampling frequency $F_s$ in Hz. In order to determine an adaptive threshold used to detect the R-peak in each ECG beat, a window size may be determined to be T, e.g., 2 seconds, based on an assumption that the slowest acceptable heart rate is 30 Beats Per Minute (BPM) that corresponds to one beat in 2 seconds. Moreover, to account for situations where only a portion of the R-peak is detected within a windowed portion in the filtered ECG signal, adjacent windowed portions are overlapped with the windowed portion by $T_0$, e.g., 0.61 seconds.

At step 604, the adaptive threshold Th for each windowed portion in the filtered ECG signal is computed based on an absolute difference signal for each windowed portion. The absolute difference signal includes an absolute value of a difference determined between ECG signals. For example, the filtered ECG signal $x_0[n]$ is passed through an absolute differentiator component (not shown), which may act as a combination of an averaging filter and a high pass filter to determine the absolute difference signal $x_1[n]$ based on Equation 3:

$$x_1[n]=|x_0[n]-x_0[n+2]| \quad (3)$$

Further, the adaptive threshold Th may be determined based on Equation 4:

$$Th=\tau * x_1[n] \quad (4)$$

In Equation 4, $\tau$ denotes a predetermined threshold value.

A z-transform $x_1(z)$ of the filtered ECG signal may be determined based on Equation 5:

$$x_1(z)=(1-z)x_0(z) \quad (5)$$

In Equation 5, $x_0(z)$ denotes a z-transform of the original ECG signal. A z-transform $x_{01}(z)$ of the filtered ECG signal may be determined using two filters based on Equation 6:

$$x_{01}(z)=(1+z^{-1})(1-z^{-1})x_0(z) \quad (6)$$

Equation 6 leads to a scaled averaging filter as $x_{avg}[n]=x_0[n]+x_0[n+1]$, and a high pass filter as $x_{hp}[n]=x_{avg}[n]-x_{avg}[n+1]$.

The absolute differentiator determines a slope between two windowed portions of the ECG signal that are separated by a single windowed portion of the ECG signal. This helps suppress an effect of an intermediate variance. The adaptive threshold is computed based on a mean of the absolute difference signal for each windowed portion due to the fact that a magnitude of the slope is required to locate the R-peak.

At step 606, a search for fiducial peaks within each windowed portion of the filtered ECG signal is performed based on the adaptive threshold value Th for each windowed portion. In more detail, the adaptive threshold value Th is used to find and eliminate the fiducial peaks, like P or T, in each ECG beat as a slope of the R-peak is substantially higher than slopes of a P wave and a T wave. Thus, a slope of a windowed portion of the filtered ECG signal that is higher than the adaptive threshold Th indicates a presence of the R-peak within the windowed portion, and may indicate a presence of the fiducial peak within the windowed portion that are less in slope than the R-peak.

At step 608, false peaks in each windowed portion of the filtered ECG signal are removed. Due to the overlapping windowed portions, the same peak may be detected twice, or a peak may straddle a boundary of a windowed portion, and as a result, a location of the peak corresponds to a maximum within the windowed portion and not an actual maximum of the R-peak. To evade false detection, locations of two consecutive peaks are determined. If a distance between the two consecutive peaks is less than a predefined value (i.e., SKIP_WINDOW), then the location of a minimum amplitude is discarded, and a location of a maximum amplitude is declared as the R-peak.

At step 610, a location of the R-peak corresponding to each ECG beat in the filtered ECG signal is detected in each windowed portion in the filtered ECG signal. In order to detect the R-peak in each windowed portion of the filtered ECG signal, samples are fiducially marked wherever a value of the absolute difference signal $x_1[n]$ crosses the adaptive threshold Th. Then, a maximum value of a peak is searched within a maximum search window (MAX_SR_WIN=0.2 sec.) of the filtered ECG signal $x_0[n]$ starting from a location of a fiducially marked sample in the respective windowed portion of the filtered ECG signal. Effectively, the maximum value represents a fiducial R-peak of a QRS complex in the respective windowed portion of the filtered ECG signal. Once the R-peak is detected, there may not be another QRS complex within an acceptable time frame (i.e., SKIP_WIN=0.25 sec.), and hence, other fiducially marked samples that come within the acceptable time frame are discarded. By discarding the other fiducially marked samples within the acceptable time frame, a computation in searching for the R-peak is significantly reduced.

Figure 7:
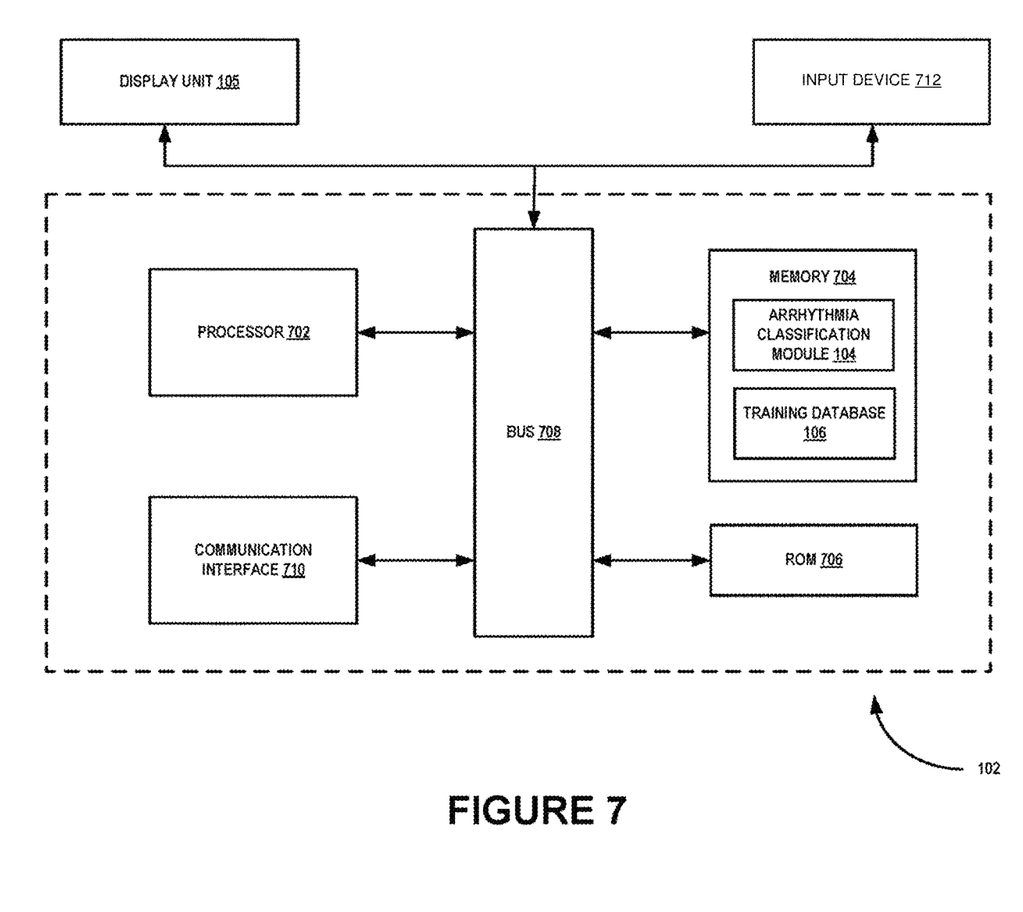
FIG. 7 is a block diagram illustrating an example of a dedicated health monitoring device of FIG. 1A.

FIG. 7 is a block diagram illustrating an example of the dedicated health monitoring device 102 of FIG. 1A. In FIG. 7, the dedicated health monitoring device 102 includes a processor 702, a memory 704, a read only memory (ROM) 706, a bus 708, a communication interface 710, the display unit 105, and an input device 712.

The processor 702 may include any type of computational circuit, such as, but not limited to, a microprocessor, a microcontroller, a complex instruction set computing microprocessor, a reduced instruction set computing microprocessor, a very long instruction word microprocessor, an explicitly parallel instruction computing microprocessor, a graphics processor, a digital signal processor, and/or any other type of processing circuit known to one of ordinary skill in the art. The processor 702 may also include embedded controllers, such as, but not limited to, generic or programmable logic devices or arrays, application specific integrated circuits, single-chip computers, smart cards, and/other controllers known to one of ordinary skill in the art.

The memory 704 and the ROM 706 may include volatile memory and non-volatile memory, respectively. The memory 704 includes the arrhythmia classification module 104 that classifies cardiac arrhythmia, using an ECG signal representing an electric activity of a heart of an individual, based on one or more examples illustrated in FIGS. 1A through 6. The memory also includes the training beat database 106 that stores training beats associated with respective arrhythmia classes. The memory 704 may include any suitable memory device(s) that stores data and machine-readable instructions, such as, but not limited to, read only memory, random access memory, erasable programmable read only memory, electrically erasable programmable read only memory, hard drive, removable media drive configured to handle compact disks, digital video disks, diskettes, magnetic tape cartridges, memory cards, and/or other memory devices known to one of ordinary skill in the art.

Examples of the subject matter may be implemented in conjunction with modules including functions, procedures, data structures, and/or application programs, which perform tasks, or define abstract data types or low-level hardware contexts. The arrhythmia classification module 104 may be stored in the form of machine-readable instructions on any of the above-mentioned storage media, and may be executable by the processor 702. For example, a computer program may include machine-readable instructions capable of classifying cardiac arrhythmia, using an ECG signal acquired from the acquisition device 108 of FIG. 1A, based on the teachings and herein described examples of the subject matter. In another example, the program may be included on a compact disk-read only memory (CD-ROM) and loaded from the CD-ROM to a hard drive in the non-volatile memory.

The communication interface 710 receives the ECG signal representing the electrical activity of the heart of the individual from the acquisition device 108 of FIG. 1A. The display unit 105 displays an arrhythmia class indicating a type of arrhythmia associated with the individual that is classified based on the ECG signal. The bus 708 acts as interconnect between various components of the dedicated health monitoring device 102. The input device 712 is well known to one of ordinary skill in the art, and hence, the explanation is thereof omitted.

The units and modules described herein may be implemented using hardware components and software components. For example, the hardware components may include microphones, amplifiers, band-pass filters, audio to digital convertors, and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more computer readable recording mediums. The computer readable recording medium may include any data storage device that can store data which can be thereafter read by a computer system or processing device. Examples of the non-transitory computer readable recording medium include read-only memory (ROM), random-access memory (RAM), CD-ROMs, magnetic tapes, floppy disks, and optical data storage devices. Also, functional programs, codes, and code segments that accomplish the examples disclosed herein can be easily construed by programmers skilled in the art to which the examples pertain based on and using the flow diagrams and block diagrams of the figures and their corresponding descriptions as provided herein.

As a non-exhaustive illustration only, a device described herein may refer to mobile devices such as a cellular phone, a personal digital assistant (PDA), a digital camera, a portable game console, and an MP3 player, a portable/personal multimedia player (PMP), a handheld e-book, a portable laptop PC, a global positioning system (GPS) navigation, a tablet, a sensor, and devices such as a desktop PC, a high definition television (HDTV), an optical disc player, a setup box, a home appliance, and the like that are capable of wireless communication or network communication consistent with that which is disclosed herein.

A computing system or a computer may include a microprocessor that is electrically connected with a bus, a user interface, and a memory controller. It may further include a flash memory device. The flash memory device may store N-bit data via the memory controller. The N-bit data is processed or will be processed by the microprocessor and N may be 1 or an integer greater than 1. Where the computing system or computer is a mobile apparatus, a battery may be additionally provided to supply operation voltage of the computing system or computer. It will be apparent to those of ordinary skill in the art that the computing system or computer may further include an application chipset, a camera image processor (CIS), a mobile Dynamic Random Access Memory (DRAM), and the like. The memory controller and the flash memory device may constitute a solid state drive/disk (SSD) that uses a non-volatile memory to store data.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of classifying cardiac arrhythmia, using an electrocardiogram (ECG) signal, the method comprising:
   receiving, from a sensor, the ECG signal representing an electrical activity of a heart of an individual over a period of time, the ECG signal comprising ECG beats;
   converting, using an arrhythmia classification hardware processor, each of the ECG beats into symbolic aggregate approximation (SAX) symbols; and
   identifying, using the arrhythmia classification hardware processor, an arrhythmia class indicating a type of cardiac arrhythmia associated with the individual from arrhythmia classes indicating respective types of cardiac arrhythmia based on the SAX symbols representing each of the ECG beats.

2. The method of claim 1, wherein the converting of each of the ECG beats comprises:
   detecting a R-peak of each of the ECG beats;
   segmenting a region of each of the ECG beats that is around the respective R-peak; and converting the region of each of the ECG beats into the SAX symbols.

3. The method of claim 1, wherein the identifying of the arrhythmia class comprises:
determining a morphology similarity measure between each of the ECG beats and training beats corresponding to the respective arrhythmia classes by comparing the SAX symbols representing each of the ECG beats and SAX symbols representing each of the training beats;
identifying an ECG beat from the ECG beats based on a training beat comprising a highest morphology similarity measure with the ECG beat;
determining whether the highest morphology similarity measure associated with the identified ECG beat is greater than a predetermined threshold value;
assigning an arrhythmia class indicating a type of cardiac arrhythmia to the identified ECG beat in response to the highest morphology similarity measure being greater than the predetermined threshold value; and
classifying the identified ECG beat as pertaining to an arrhythmia class that corresponds to the training beat associated with the highest morphology similarity measure in response to the highest morphology similarity measure being less than or equal to the predetermined threshold value.

4. The method of claim 1, wherein the identifying of the arrhythmia class comprises:
determining a frequency of occurrence of the SAX symbols representing each of the ECG beats; and
classifying each of the ECG beats as belonging to one of clusters of ECG beats based on the frequency of occurrence of the SAX symbols representing each of the ECG beats, the clusters of ECG beats corresponding to the respective arrhythmia classes.

5. A health monitoring device comprising:
a communication interface configured to receive an electrocardiogram (ECG) signal from a sensor representing an electrical activity of a heart of an individual over a period of time, the ECG signal comprising ECG beats; and
an arrhythmia classification hardware module configured to
convert each of the ECG beats into symbolic aggregate approximation (SAX) symbols, and
identify an arrhythmia class indicating a type of cardiac arrhythmia associated with the individual from arrhythmia classes indicating respective types of cardiac arrhythmia based on the SAX symbols representing each of the ECG beats.

6. The health monitoring device of claim 5, wherein the arrhythmia classification hardware module comprises:
a display module configured to display the arrhythmia class.

7. The health monitoring device of claim 5, wherein the arrhythmia classification hardware module comprises:
a band pass filter configured to filter the ECG signal.

8. The health monitoring device of claim 5, wherein the arrhythmia classification hardware module comprises:
a R-peak detection module configured to detect a R-peak of each of the ECG beats.

9. The health monitoring device of claim 8, wherein the arrhythmia classification hardware module comprises:
a symbolic aggregate approximation module configured to segment a region of each of the ECG beats that is around the respective R-peak, and
convert the region of each of the ECG beats into the SAX symbols.

10. The health monitoring device of claim 5, wherein the arrhythmia classification hardware module comprises:
a arrhythmia class identification module configured to
determine a morphology similarity measure between each of the ECG beats and training beats corresponding to the respective arrhythmia classes by comparing the SAX symbols representing each of the ECG beats and SAX symbols representing each of the training beats,
identify an ECG beat from the ECG beats based on a training beat comprising a highest morphology similarity measure with the ECG beat,
determine whether the highest morphology similarity measure associated with the identified ECG beat is greater than a predetermined threshold value,
assign an arrhythmia class indicating a type of cardiac arrhythmia to the identified ECG beat in response to the highest morphology similarity measure being greater than the predetermined threshold value, and
classify the identified ECG beat as pertaining to an arrhythmia class that corresponds to the training beat associated with the highest morphology similarity measure in response to the highest morphology similarity measure being less than or equal to the predetermined threshold value.

11. The health monitoring device of claim 10, wherein the arrhythmia class identification module is further configured to:
store the identified ECG beat assigned with the arrhythmia class.

12. The health monitoring device of claim 5, wherein the arrhythmia classification hardware module comprises:
a arrhythmia class identification module configured to
determine a frequency of occurrence of the symbols representing each of the ECG beats, and
classify each of the ECG beats as belonging to one of clusters of ECG beats based on the frequency of occurrence of the symbols representing each of the ECG beats.

13. The health monitoring device of claim 12, wherein the clusters of ECG beats correspond to the respective arrhythmia classes.

14. The health monitoring device of claim 5, wherein the arrhythmia classes comprise normal, or left bundle brunch block, or right bundle brunch block, or atrial premature beat, or premature ventricular contraction, or any combination thereof.

15. A system comprising:
an acquisition device configured to generate an electrocardiogram (ECG) signal representing an electrical activity of a heart of an individual over a period of time, the ECG signal comprising ECG beats; and
a health monitoring hardware device configured to
convert each of the ECG beats into symbolic aggregate approximation (SAX) symbols, and
identify an arrhythmia class indicating a type of cardiac arrhythmia associated with the individual from arrhythmia classes indicating respective types of cardiac arrhythmia based on the SAX symbols representing each of the ECG beats.

16. The system of claim 15, wherein the health monitoring hardware device is further configured to:
display the arrhythmia class on a display panel.

17. The system of claim 15, wherein the health monitoring device is further configured to:
filter the ECG signal using a filter.

18. The system of claim 15, wherein the health monitoring hardware device is further configured to:
   detect a R-peak of each of the ECG beats;
   segment a region of each of the ECG beats that is around the respective R-peak; and
   convert the region of each of the ECG beats into the SAX symbols.

19. The system of claim 15, wherein the health monitoring hardware device is further configured to:
   determine a morphology similarity measure between each of the ECG beats and training beats corresponding to the respective arrhythmia classes by comparing the symbols representing each of the ECG beats and symbols representing each of the training beats;
   identify an ECG beat from the ECG beats based on a training beat comprising a highest morphology similarity measure with the ECG beat;
   determine whether the highest morphology similarity measure associated with the identified ECG beat is greater than a predetermined threshold value;
   assign an arrhythmia class indicating a type of cardiac arrhythmia to the identified ECG beat in response to the highest morphology similarity measure being greater than the predetermined threshold value; and
   classify the identified ECG beat as pertaining to an arrhythmia class that corresponds to the training beat associated with the highest morphology similarity measure in response to the highest morphology similarity measure being less than or equal to the predetermined threshold value.

20. The system of claim 15, wherein the health monitoring hardware device is further configured to:
   determine a frequency of occurrence of the symbols representing each of the ECG beats; and
   classify each of the ECG beats as belonging to one of clusters of ECG beats based on the frequency of occurrence of the SAX symbols representing each of the ECG beats, the clusters of ECG beats corresponding to the respective arrhythmia classes.

21. The method of claim 4, wherein the clusters comprise normal ECG beats, premature ventricular contraction (PVC) ECG beats, and atrial premature complex (APC) ECG beats.

* * * * *